(12) United States Patent
Bayer et al.

(10) Patent No.: US 7,153,469 B2
(45) Date of Patent: *Dec. 26, 2006

(54) FOUR EDGE SEALED STERILIZATION WRAP AND METHOD FOR STERILIZING AN ARTICLE

(75) Inventors: Robert T. Bayer, Asheville, NC (US); Brian G. Hoge, Fletcher, NC (US); David G. Pasternack, Asheville, NC (US); William F. Church, Weaverville, NC (US); James F. Whitaker, Alexander, NC (US); Stephen R. Everson, Arden, NC (US)

(73) Assignee: Cardinal Health 200, Inc., Dublin, OH (US)

( * ) Notice: Subject to any disclaimer, the term of this patent is extended or adjusted under 35 U.S.C. 154(b) by 129 days.

This patent is subject to a terminal disclaimer.

(21) Appl. No.: 10/911,316

(22) Filed: Aug. 3, 2004

(65) Prior Publication Data

US 2005/0008527 A1    Jan. 13, 2005

Related U.S. Application Data

(60) Continuation of application No. 10/119,183, filed on Apr. 9, 2002, now Pat. No. 6,793,879, which is a division of application No. 09/451,056, filed on Nov. 30, 1999, now Pat. No. 6,517,916.

(51) Int. Cl.
*A61L 2/00* (2006.01)

(52) U.S. Cl. .............................. 422/1; 53/425; 53/466; 53/467; 422/28; 422/40; 428/36.1

(58) Field of Classification Search .................... 422/1, 422/28, 40; 53/425, 466, 467; 428/36.1

See application file for complete search history.

(56) References Cited

U.S. PATENT DOCUMENTS

| | | | |
|---|---|---|---|
| 3,761,013 A | 9/1973 | Schuster | 206/439 |
| 3,780,857 A | 12/1973 | Rosano, Jr. et al. | 206/370 |
| 4,196,245 A | 4/1980 | Kitson et al. | 428/198 |
| 4,201,031 A | 5/1980 | Wiles | 53/459 |
| 4,342,392 A | 8/1982 | Cox | 206/438 |
| 4,581,874 A | 4/1986 | Rechtsteiner et al. | 53/459 |
| 4,644,586 A | 2/1987 | Padgett | 383/102 |
| 4,644,732 A | 2/1987 | Morton | 383/121 |
| 4,863,785 A | 9/1989 | Berman et al. | 428/218 |
| 5,072,832 A | 12/1991 | Valentine et al. | 206/570 |
| 5,635,134 A | 6/1997 | Bourne et al. | 422/26 |

(Continued)

*Primary Examiner*—Krisanne Jastrzab
(74) *Attorney, Agent, or Firm*—Carter, Schnedler, & Monteith

(57) ABSTRACT

There is provided an improved sterilization wrap and a method for using the improved sterilization wrap to sterilize an article. The wrap is made of first and second sheets of sterilization material. Each sheet has first, second, third and fourth edges. Each sheet includes a central portion. The first edge of the first sheet is in register with and bonded to the first edge of the second sheet; the second edge of the first sheet is in register with and bonded to the second edge of the second sheet; the third edge of the first sheet is in register with and bonded to the third edge of the second sheet; and the fourth edge of the first sheet is in register with and bonded to the fourth edge of the second sheet. The central portions of the first and second sheets are substantially not bonded together. Thus, two layers of sterilization material are provided for an article to be sterilized.

18 Claims, 3 Drawing Sheets

U.S. PATENT DOCUMENTS

| | | | |
|---|---|---|---|
| 5,673,541 A | 10/1997 | Arzuman et al. | 53/459 |
| 5,688,476 A | 11/1997 | Bourne et al. | 422/294 |
| 5,879,620 A | 3/1999 | Cohen | 206/439 |
| 6,406,764 B1 * | 6/2002 | Bayer | 428/35.2 |
| 6,793,879 B1 * | 9/2004 | Bayer et al. | 422/1 |

* cited by examiner

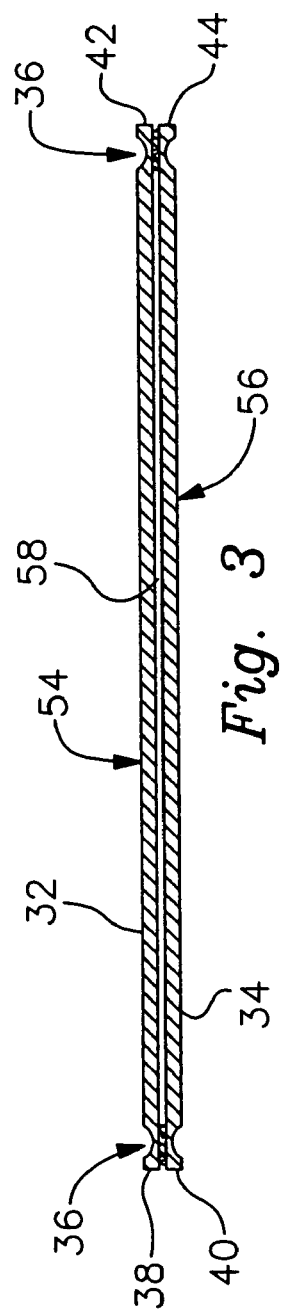
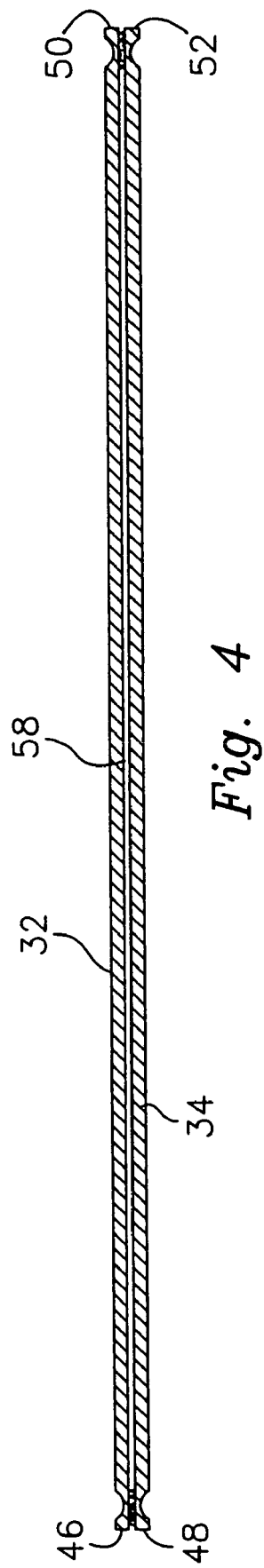
Fig. 3
Fig. 4

FOUR EDGE SEALED STERILIZATION WRAP AND METHOD FOR STERILIZING AN ARTICLE

RELATIONSHIP TO PRIOR APPLIATION

This application is a continuation of U.S. patent application Ser. No. 10/119,183 filed Apr. 9, 2002 now U.S. Pat. No. 6,793,879 and titled FOUR EDGE SEALED STERILIZATION WRAP AND METHOD FOR STERILIZING AN ARTICLE. Application Ser. No. 10/119,183 is a divisional of U.S. patent application Ser. No. 09/451,056, filed Nov. 30, 1999, which issued as U.S. Pat. No. 6,517,916 on Feb. 11, 2003 and is titled FOUR EDGE SEALED STERILIZATION WRAP AND METHOD FOR STERILIZING AN ARTICLE.

BACKGROUND OF THE INVENTION

This invention relates to sterilization wrap. More particularly, it relates to sterilization wrap having two sheets of sterilization material.

Reusable medical instruments must be sterilized prior to each use. Normally, these instruments are sterilized by steam or ethylene-oxide. In order for the instruments to remain sterile after the sterilization procedure, the instruments must be wrapped in a material called "sterilization wrap".

The most common type of sterilization wrap is a three-ply laminate consisting of a layer of melt blown polypropylene sandwiched between two layers of spun bond polypropylene. The wrap includes bond points all across the face of the material so that the material is held together, i.e., laminated. This three-ply material is commonly referred to as "SMS", which is short for spun bond—melt blown—spun bond. Most hospitals specify SMS as the sterilization wrap to be used because SMS is sufficiently porous to permit steam, ethylene-oxide and other sterilization materials to penetrate through the material to the surgical instruments, but has filtration properties sufficient to prevent the passage of most pathogens there through and maintain sterility after the sterilization process. The wrap also protects articles during sterilization, and acts as a filtration medium for the sterilant.

In most hospitals, there is a protocol which requires surgical instruments to be wrapped with two separate sheets of SMS so that in the event one sheet becomes torn, there is a redundancy which will maintain the sterility of the surgical instruments. The wrapping of surgical instruments with two separate sheets of sterilization wrap obviously is labor intensive in that the nurse must first place the instruments on one sheet of sterilization material and wrap the instruments, and then place the wrapped package on another sheet of sterilization material and wrap the package containing the instruments.

In an attempt to reduce the labor required to provide dual wrapping of surgical instruments, Kimberly-Clark Corporation has developed a product called "One Step Sterilization Wrap". One Step Sterilization Wrap is made by bonding two separate sheets of sterilization wrap together near two of the edges of the adjacent sheets. The Kimberly-Clark One Step product is described in U.S. Pat. Nos. 5,635,134 and 5,688,476.

FIG. 1 shows one of the Kimberly-Clark One Step products described in these Kimberly-Clark patents. Sterilization wrap 10 includes a top layer 12 made of SMS and a bottom layer 14 also made of SMS. The two layers of SMS are bonded together near two opposing edges 16 and 18, as illustrated by bond lines 20 and 22. The method of bonding the two sheets together may be ultrasonic bonding. The other two opposing edges 24 and 26 are not bonded together so there is a visible gap 28 between sheets 12 and 14 so that the user of the sterilization wrap visually distinguishes the fact that there are, indeed, two sheets. Apparently the purpose for insuring that the two sheets are visually distinguishable as separate sheets is so that the user will know with certainty that the item to be sterilized has two sheet protection. However, because of this gap 28, debris could enter the region between the two sheets. With two of the edges being unbonded, it is possible that the sheets will become misaligned so that if a sharp object penetrates both sheets, the resulting holes in each sheet could also become misaligned, thus reducing ones ability to determine whether or not there is a hole through both sheets. In addition, since edges 24 and 26 are not bonded and bond lines 20 and 22 are somewhat removed from edges 16 and 18, fibers from those edges could become released from the wrap. Also, since the edges 24 and 26 are not bonded, the two sheets might be pulled apart by mistake during use. Furthermore, since the wrap shown in FIG. 1 is not sealed right to the edges 16 and 18, the user might perceive that there could be contamination between the sheets. Thus, there is a need for a sterilization wrap which provides two layers of protection and which overcomes the problems of the prior art.

OBJECTS OF THE INVENTION

It is therefore one object of this invention to provide an improved two-sheet sterilization wrap.

It is another object of this invention to provide a two-sheet sterilization wrap which is easy to use.

It is still another object of this invention to provide an improved two-sheet sterilization wrap which is less likely to be contaminated and is less likely to be pulled apart.

It is yet another object of this invention to provide a method for sterilizing an article utilizing an improved two-sheet sterilization wrap.

It is still another object of this invention to provided a two sheet sterilization wrap which eliminates confusion by the user regarding the number of sheets in each wrap.

BRIEF SUMMARY OF THE INVENTION

In accordance with one form of this invention, there is provided a sterilization wrap made from two sheets of sterilization material. Each sheet has first, second, third and fourth edges. Each sheet includes a central portion. The first edge of the first sheet is in register with and bonded to the first edge of the second sheet. The second edge of the first sheet is in register with and bonded to the second edge of the second sheet. The third edge of the first sheet is in register with and bonded to the third edge of the second sheet. The fourth edge of the first sheet is registered with and bonded to the fourth edge of the second sheet. The central portions of each sheet are substantially not bonded together. Thus two layers of sterilization material is provided for the article to be sterilized. The region between the central portion of each sheet is protected from contaminates and the bonded edges of the wrap are readily grasped by the person wrapping the articles to be sterilized.

In accordance with another form of this invention, there is provided a method for sterilizing an article, including the step of providing the article, wrapping the article with sterilization wrap made in accordance with the above-described design, and applying sterilization conditions to the wrapped article.

BRIEF DESCRIPTION OF THE DRAWINGS

The subject matter which is regarded as the invention is set forth in the appended claims. The invention itself, however, together with further objects and advantages thereof may be better understood in reference to the accompanying drawings in which:

FIG. 3 is a sectional view of the sterilization wrap of FIG. 2 taken through Section Lines 3—3;

FIG. 4 is sectional view of the sterilization wrap of FIG. 2 taken through Section Lines 4—4;

DETAILED DESCRIPTION OF THE PREFERRED EMBODIMENTS

Figure 1:
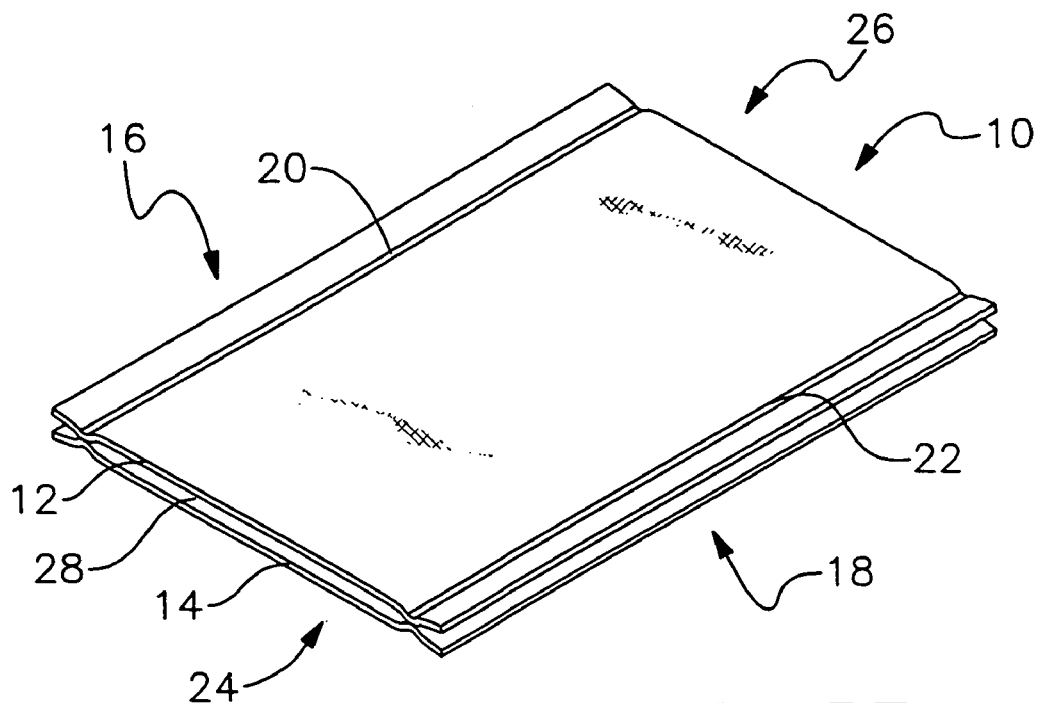
FIG. 1 is a perspective view of a prior art sterilization wrap.

Referring now more particularly to FIGS. 2 through 5, there is provided a sterilization wrap in the form of application 30 which is made of two sheets of sterilization material 32 and 34. Each sheet of sterilization material is preferably a three ply laminate having a layer of melt blown polypropylene sandwiched between two layers of spun bonded polypropylene, referred to as SMS. SMS is commercially available from BBA Nonwovens Company. Alternatively, each sheet could be made of two bonded layers of medical grade paper CSR, a combination of paper CSR and SMS, a combination of tissue, polyethylene (or polypropylene) and tissue, and other known sterilization materials.

Sheet 32 is the same size as sheet 34, and the two sheets are in register with one another and are joined together by bonding the two sheets along all four of their respective edges, as illustrated by bond points 36.

As shown in FIG. 3, edge 38 of sheet 32 is bonded to edge 40 of sheet 34. Edge 42 of sheet 32 is bonded to edge 44 of sheet 34. As shown in FIG. 4, edge 46 of sheet 32 is bonded to edge 48 of sheet 34. Edge 50 of sheet 32 is bonded to edge 52 of sheet 34. The central region 54 of sheet 32 in not substantially bonded to the central region 56 of sheet 34. This results in open space 58 occurring between sheet 32 and sheet 34.

Figure 2:
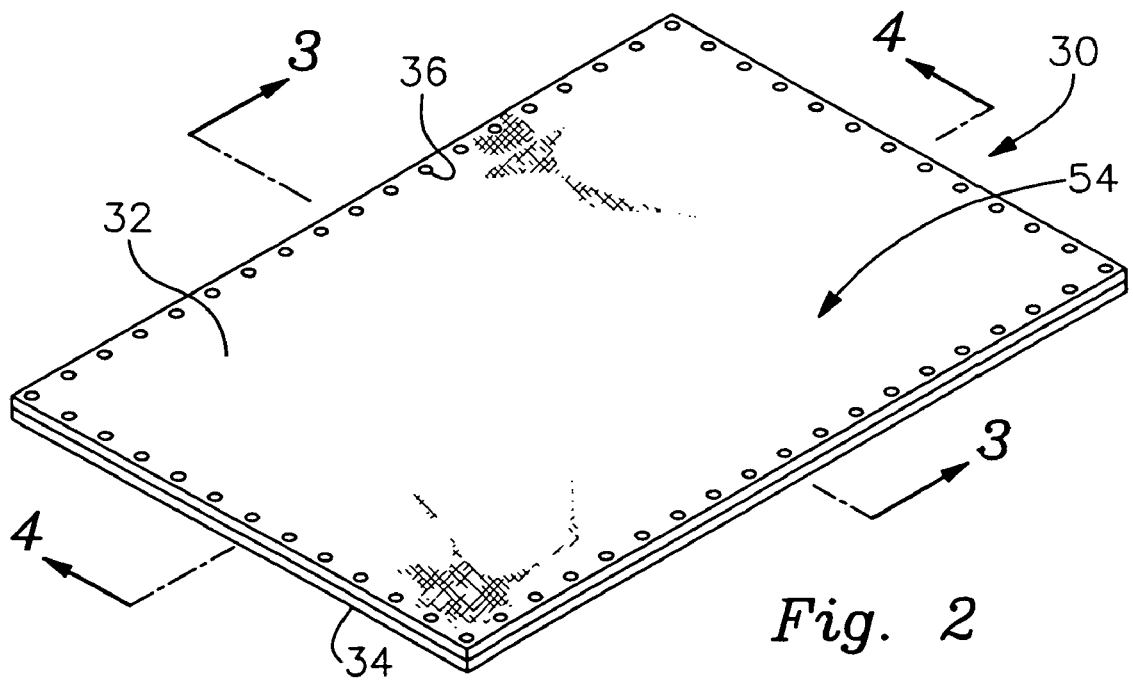
FIG. 2 is a perspective view of the sterilization wrap, in accordance with this subject invention.
Figure 5:
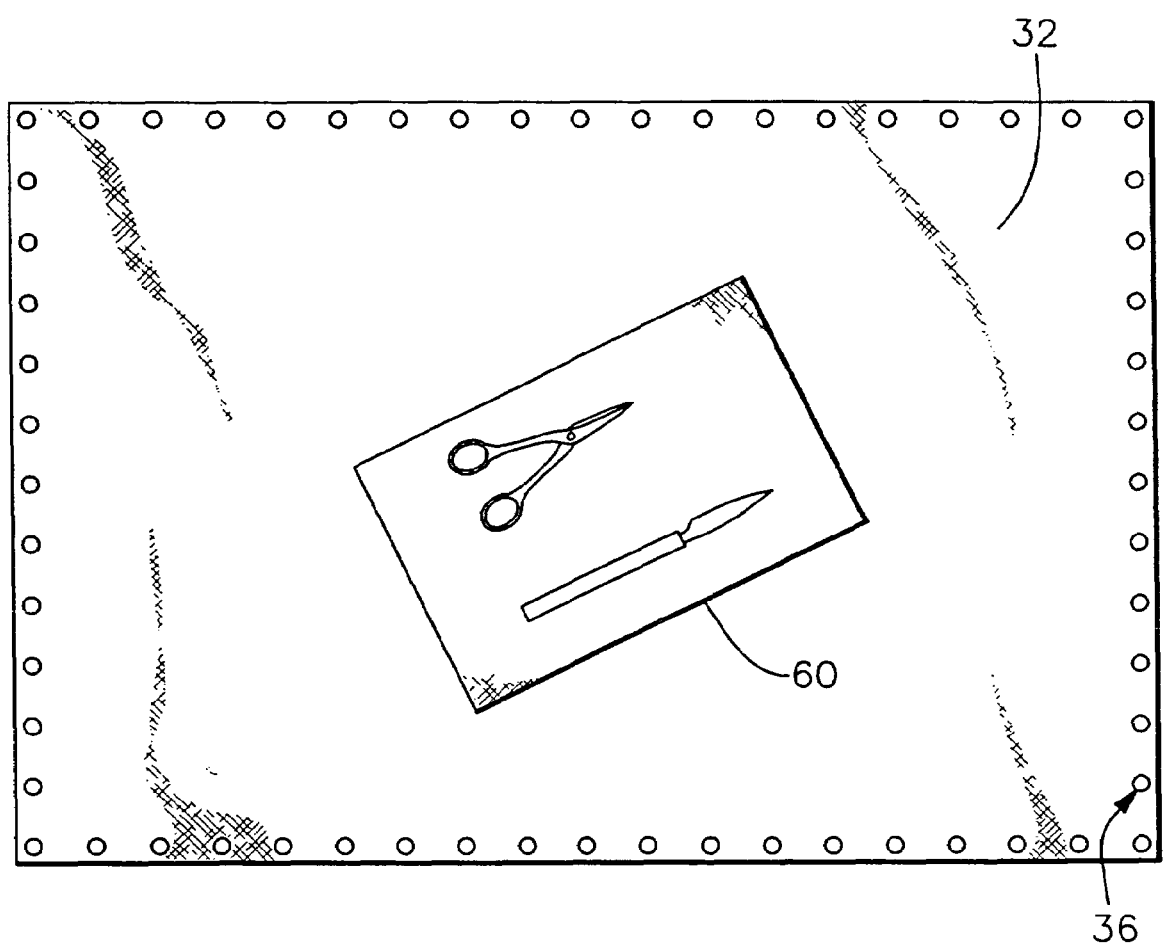
FIG. 5 is a plan view of the sterilization wrap of FIG. 2 showing the materials to be sterilized in preparation for wrapping.

The bond points 36 along the edges of each sheet are preferably at the very end of the edges of each sheet. This will substantially reduce the likelihood that fibers from free edges will be released since the bonding process melts the fibers at the bond points. The bond points illustrated in FIG. 2 show the bond points spaced apart for illustrative purposes only. Actually, the bond points are very close together.

The central region 54 of sheet 32 and central region 56 of sheet 34 remain substantially not bonded together so that the passage of the sterilization materials through the wrap to the articles 60 to be sterilized is not substantially reduced by the points. That is, thermal bonding of the two sheets together in their central regions 54 and 56 will melt the SMS, resulting in a film like structure which would block the passage of a substantial amount of ethylene oxide or steam, which are the preferred sterilization materials.

Since the sterilization wrap is bonded along all four edges, the wrap will not be visually distinguishable as two separate sheets. However, a significant advantage of the two sheets being bonded together along all four edges is the fact that debris will not be permitted to penetrate into the open space 58 since all four edges, in effect, are sealed. In addition, since the bonding occurs directly adjacent to the edges, or even overlapping the edges, loss of fibers about the edges is substantially reduced. Furthermore, since all four edges are bonded together, the likelihood that the two sheets will stay together is substantially enhanced. Also, since the bond of all four edges occurs directly adjacent to the edges, there should be no user perception that there might be contamination between the sheets and/or that the sterilization materials might escape.

The sterilization wrap of the subject invention, with the two sheets bonded together on the edges, also provides a reasonable rigid edge which is easily grasped by the person using the sterilization wrap.

One of the methods of bonding is ultrasonic bonding which results in bond points. Alternatively, hot melt glue, a heated knife or wire, laser, water jet, thermo-mechanism, or mechanical embossing may be used to create the bonding.

The sterilization wrap of the subject invention is easy to manufacture. Two identical size sheets are cut into the desired shape, most commonly square shape. The two sheets are placed in register, and then all four edges are bonded together by one of the bonding techniques referred to above.

By utilizing this invention, there is no need for the user to handle two separate sheets of sterilization wrap in order to provide two layers of protection for the articles to be sterilized. A single application 30 is removed from its container and placed flat on a table. The article to be sterilized is placed in the center of the wrap/application 30. The article is then wrapped in the generally prescribed or acceptable fashion. The wrapped article is placed in an autoclave or gas enclosure and is subjected to sterilizing conditions.

From the foregoing description of the preferred embodiments of the invention, it will be apparent that many modifications may be made therein. It will be understood, however, that the embodiments of the invention are an exemplification of the invention only and that the invention is not limited thereto. It is to be understood, therefore, that it is intended in the appended claims to cover all modifications as fall within the true spirit and scope of the invention.

What is claimed is:

1. A method for sterilizing an article utilizing sterilization material which includes first and second layers of sterilization material; each layer having first, second, third and fourth edges; each layer having a central portion;

said first edge of said first layer being in register with and joined to said first edge of said second layer;

said second edge of said first layer being in register with and joined to said second edge of said second layer;

said third edge of said first layer being in register with and joined to said third edge of said second layer;

said fourth edge of said first layer being in register with and joined to said fourth edge of said second layer;

said central portion of said first layer not substantially joined to said central portion of said second layer;

said first layer having an outer surface;

said first layer having an inner surface;

an open space between said central portions of each layer; said open space being substantially sealed by the joining along said edges of said layers;

said method comprising the steps of:

providing an article to be sterilized; said article to be sterilized being at least one re-usable medical instrument;

positioning said article to be sterilized above the outer surface of said first layer;

said inner surface of said first layer not contacting said article to be sterilized;

wrapping said article to be sterilized with said first and second layers;

applying sterilization conditions to said wrapped article whereby two layers of sterilization material are provided for said article to be sterilized.

2. A method as set forth in claim 1 wherein said sterilization material is SMS.

3. A method as set forth in claim 1 wherein said sterilization material is taken from the group consisting of SMS, two bonded layers of medical grade paper, the combination of medical grade paper and SMS, the combination of tissue, polyethylene and tissue, and the combination of tissue, polypropylene and tissue.

4. A method as set forth in claim 1 wherein the adjacent edges of each layer do not diverge from one another.

5. A method as set forth in claim 1 wherein the edges are continuously joined.

6. A method as set forth in claim 1 wherein said layers are separate sheets.

7. A method for sterilizing an article utilizing sterilization material which includes
   an article to be sterilized; said article to be sterilized being at least one re-usable medical instrument;
   first and second layers of sterilization material; each layer having first, second, third and fourth edges; each layer having a central portion;
   said first edge of each layer being in register and joined together;
   said second edge of each layer being in register and joined together;
   said third edge of each layer being in register and joined together;
   said fourth edge of each layer being in register and joined together;
   said first layer having an outer surface;
   said first layer having an inner surface;
   said central portion of said first layer not substantially joined to said central portion of said second layer;
   an open space between said central portions of each layer, wherein said open space is substantially sealed by the joining along the edges of said layers so that the region between said central portions of each layer is substantially protected from contaminants;
   a method comprising the steps of:
      providing an article to be sterilized; said article to be sterilized being at least one re-usable medical instrument;
      positioning said article to be sterilized above the outer surface of said first layer;
      said inner surface of said first layer not contacting said article to be sterilized;
      wrapping said article to be sterilized by said first and second layers;
      applying sterilization conditions to the wrapped article whereby two layers of sterilization material are provided for said article to be sterilized.

8. A method as set forth in claim 7 wherein said sterilization material is SMS.

9. A method as set forth in claim 7 wherein said sterilization material is taken from the group consisting of SMS, two bonded layers of medical grade paper, the combination of medical grade paper and SMS, the combination of tissue, polyethylene and tissue, and the combination of tissue, polypropylene and tissue.

10. A method as set forth in claim 7 wherein the adjacent edges of each layer do not diverge from one another.

11. A method as set forth in claim 7 wherein said first, second, third and fourth edges of said first layer are continuously joined to respective first, second, third and fourth edges of said second layer.

12. A method as set forth in claim 7 wherein said layers are separate sheets.

13. A method for sterilizing an article utilizing sterilization material which includes
   first and second layers of sterilization material; each layer having first, second, third and fourth edges; each layer having a central portion;
   said first edge of each layer being in register and joined together;
   said second edge of each layer being in register and joined together;
   said third edge of each layer being in register and joined together;
   said fourth edge of each layer being in register and joined together;
   said central portion of each layer being substantially not joined together; said edges being readily grasped by a person using the sterilization material;
   said first layer having an outer surface;
   said first layer having an inner surface;
   an open space between said central portions of each layer;
   said open space being substantially sealed by the joining along the edges of said layers;
   said method comprising the steps of:
      providing an article to be sterilized; said article to be sterilized being at least one re-usable medical instrument;
      positioning said article to be sterilized above the outer surface of said first layer;
      said inner surface of said first layer not contacting said article to be sterilized;
      wrapping said article to be sterilized with said first and second layers of sterilization material;
      applying sterilization conditions to the wrapped article whereby two layers of sterilization material are provided for said article to be sterilized.

14. A method as set forth in claim 13 wherein said sterilization material is SMS.

15. A method as set forth in claim 13 wherein said sterilization material is taken from the group consisting of SMS, two bonded layers of medical grade paper, the combination of medical grade paper and SMS, the combination of tissue, polyethylene and tissue, and the combination of tissue, polypropylene and tissue.

16. A method as set forth in claim 13 wherein the adjacent edges of said layers do not diverge from one another.

17. A method as set forth in claim 13 wherein said first, second, third and fourth edges of said first layer are substantially continuously joined.

18. A method as set forth in claim 13 wherein said layers are separate sheets.

* * * * *